(12) United States Patent  
Barlage et al.

(10) Patent No.: US 8,637,687 B2
(45) Date of Patent: Jan. 28, 2014

(54) PROCESS FOR MAKING AMIDES

(71) Applicant: BASF SE, Ludwigshafen (DE)

(72) Inventors: Wilhelm Barlage, Leverkusen (DE); Javier Raya, Sant Joan Despi (ES); Joaquin Bigorra Llosas, Sabadell (ES); Harald Rößler, Düsseldorf (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/847,019

(22) Filed: Mar. 19, 2013

(65) Prior Publication Data

US 2013/0245297 A1 Sep. 19, 2013

Related U.S. Application Data

(60) Provisional application No. 61/612,452, filed on Mar. 19, 2012.

(51) Int. Cl.
C07C 231/00 (2006.01)

(52) U.S. Cl.
USPC ............................................ 554/69; 564/138

(58) Field of Classification Search
USPC ............................................ 554/69; 564/138
See application file for complete search history.

(56) References Cited

FOREIGN PATENT DOCUMENTS

| WO | WO-2005/095320 | 10/2005 | |
|----|----------------|---------|---|
| WO | WO-2010/108814 | 9/2010 | |
| WO | WO 2010108814 A1 * | 9/2010 | ............ C07C 231/02 |

OTHER PUBLICATIONS

"Extended European Search Report in 12160173.6-1211", dated Sep. 13, 2012, 4 pgs.
Rao, J. L. et al., "Cathodically Electrodepositable Novel Coating System from Castor Oil", Journal of Applied Polymer Science, vol. 44 1992, pp. 1873-1881.

* cited by examiner

Primary Examiner — Deborah D Carr
(74) Attorney, Agent, or Firm — Servilla Whitney LLC

(57) ABSTRACT

Provided are processes for making an amide of a carboxylic acid by reacting an amine of the formula (I)

$$H\text{—}NR^1R^2 \qquad (I)$$

wherein $R^1$ and $R^2$ are the same or different, $R^1$ comprising a $C_1$-$C_4$-alkyl, and $R^2$ comprising hydrogen or a $C_1$-$C_4$-alkyl, the amine having a lower boiling point than water, with a carboxylic acid with at least 3 carbon atoms per molecule, said carboxylic acid optionally comprising at least one alcoholic hydroxyl group per molecule, and selecting a molar ratio of amine to carboxylic acid in the range of from 1.5:1 to 1:1.

The reaction step occurs under
- temperature and pressure conditions at which water and amine according to formula (I) are gaseous, and in a single reactor,
- the water formed together with any unreacted amine is distilled off, any unreacted amine is separated from the water and said the unreacted amine is reintroduced into the reaction mixture.

10 Claims, No Drawings

PROCESS FOR MAKING AMIDES

CROSS-REFERENCE TO RELATED APPLICATIONS

This application claims the benefit under 35 U.S.C. §119 (e) to U.S. Provisional Application No. 61/612,452, filed Mar. 19, 2012, which is incorporated herein by reference in its entirety.

FIELD

The present invention is directed towards a process for making an amide of a carboxylic acid by reacting an amine of the formula (I)

$$H—NR^1R^2 \qquad (I)$$

$R^1$ and $R^2$ being defined as being the same or different,
$R^1$ being selected from $C_1$-$C_4$-alkyl,
$R^2$ being selected from hydrogen and $C_1$-$C_4$-alkyl,
$R^1$ and $R^2$ being combined in a way that amine according to formula (I) has a lower boiling point than water,
with a carboxylic acid with at least 3 carbon atoms per molecule, said carboxylic acid optionally bearing at least one alcoholic hydroxyl group per molecule,
selecting a molar ratio of amine according to formula (I) to carboxylic acid in the range of from 1.5:1 to 1:1,
comprising the following measures during the reaction step:
(a) reacting amine according to formula (I) with said carboxylic acid at temperature and pressure conditions at which water and amine according to formula (I) are gaseous, wherein the reaction (a) is performed in a single reactor,
(b) distilling off the water formed, together with unreacted amine according to formula (I),
(c) separating unreacted amine according to formula (I) from the water and
(d) re-introducing said amine according to formula (I) into the reaction mixture in measure (a).

BACKGROUND

Fatty acid alkyl amides and dialkyl amides are used for various applications such as environmentally friendly solvents and as manufacturing aid for polymers. Processes for manufacturing of such amides are known in the art. Many of them start off from a carboxylic acid or a derivative such as the respective halide or ester and an alkyl or dialkyl amide. However, several drawbacks can be observed. Carboxylic acid halides, however, are expensive, and they tend to cleave off hydrogen halides during various occasions such as storing, transport, and reactions. Such halides are highly corrosive, and during the amide formation they need to be neutralized, either by one equivalent of amine or by an added base which may also react with carboxylic acid halide instead.

During formation of amides from esters (or lactones) and amines, alcohols will be formed, reducing the corrosion problem described above, see, e. g., WO 2010/037776. However, esters and lactones are usually quite expensive compared to carboxylic acids.

In US 2009/0062565, a process is disclosed in which fatty acid amides are being produced from the respective carboxylic acid and an amine. The process disclosed makes use of a two-reactor system. The water formed is being distilled off together with amine, and after a separation the amine can be recycled by introducing it into acid in order to start the amide formation reaction. However, for this process, usually an excess of amine is needed. This is particularly disadvantageous for small scale production and discontinuous processes.

SUMMARY

Embodiments of the present invention provide a process for making carboxylic acid amides from carboxylic acids that does not require a major excess of amine but yields amides in high yields and good purity.

Accordingly, the process defined at the outset was found, hereinafter also being referred to as the inventive process.

DETAILED DESCRIPTION

In the course of the inventive process a carboxylic acid, also being referred to as carboxylic acid (II), will be reacted with an amine of the formula (I)

$$H—NR^1R^2 \qquad (I),$$

briefly also referred to as amine (I), $R^1$ and $R^2$ being defined as being different or preferably identical,
$R^1$ being selected from $C_1$-$C_4$-alkyl, such as methyl, ethyl, n-propyl, iso-propyl, n-butyl, iso-butyl, sec.-butyl, or tert.-butyl, preferably n-$C_1$-$C_4$-alkyl and particularly methyl or ethyl,
$R^2$ being selected from hydrogen and $C_1$-$C_4$-alkyl, such as methyl, ethyl, n-propyl, iso-propyl, n-butyl, iso-butyl, sec.-butyl, or tert.-butyl, preferably n-$C_1$-$C_4$-alkyl and particularly methyl or ethyl,
wherein $R^1$ and $R^2$ are being combined in a way that amine according to formula (I) has a lower boiling point than water.

In one embodiment of the present invention, water and amine according to formula (I) are selected from methylamine, dimethylamine, ethylamine, diethylamine, n-propylamine, isopropylamine, diisopropylamine, n-butylamine, iso-butylamine, tert-butylamine, methyl n-propylamine, n-methyl-n-ethyl amine and methyl iso-propylamine. Particularly preferred amines of formula (I) are selected from dimethylamine and diethylamine.

Carboxylic acids that will be reacted according to the inventive process are being selected from carboxylic acids with at least 3 carbon atoms per molecule, said carboxylic acid optionally bearing at least one alcoholic hydroxyl group per molecule.

In one embodiment of the present invention, carboxylic acid (II) is selected from $C_3$-$C_{18}$-carboxylic acids that are branched and non-substituted, such as isobutyric acid and isovaleric acid.

In one embodiment of the present invention, carboxylic acid (II) is selected from $C_3$-$C_{18}$-carboxylic acids that are preferably straight chain and non-substituted. Examples are propionic acid, butyric acid, valeric acid, caproic acid (n-$C_5H_{11}$—COOH), caprylic acid, capric acid, lauric acid, myristic acid, palmitic acid, and stearic acid. Carboxylic acid (II) may have one or more carbon-carbon double bonds that are non-conjugated with the carboxylic acid group. Preferred are carboxylic acids that do not have a carbon-carbon double bond.

In one particularly preferred embodiment of the present invention, carboxylic acid (II) is selected from caprylic acid, capric acid and lauric acid and amine (I) is selected from dimethylamine and diethylamine.

In one embodiment of the present invention, carboxylic acid (II) is selected from α-hydroxyl $C_3$-$C_{12}$-carboxylic acids that are preferably straight-chain. Particularly preferred are α-hydroxyl $C_3$-$C_{12}$-carboxylic acids which bear no additional functional groups.

In case carboxylic acid (II) is chiral, e. g., α-hydroxyl $C_3$-$C_{12}$-carboxylic acids being selected as carboxylic acid (II), it has been found that the stereochemistry does not have an influence on the reaction. Thus, any enantiomer as well as the racemate can be used as starting material.

In one embodiment of the present invention, carboxylic acid (II) is selected from lactic acid.

In one particularly preferred embodiment of the present invention, carboxylic acid (II) is selected from lactic acid and amine (I) is selected from dimethylamine and diethylamine.

In the inventive process, a molar ratio of amine (I) to carboxylic acid (II) in the range of from 1.5:1 to 1:1 will be selected, referring to the overall ratio of starting materials, preferably of from 1.2:1 to 1:1.

The inventive process comprises the following measures during the reaction step:
(a) reacting amine according to formula (I) with carboxylic acid (II) at temperature and pressure conditions at which water and amine (I) are gaseous, wherein the reaction (a) is performed in a single reactor,
(b) distilling off the water formed, together with unreacted amine (I),
(c) separating unreacted amine according to formula (I) from the water and
(d) re-introducing said amine (I) into the reaction mixture in measure (a).

Measures (a) to (d) will be discussed in more detail below.

The term "measure" in the context of the present invention does not necessarily imply that the different measures are being carried out consecutively. For example, re-introduced amine (I) according to measure (d) will again be reacted with carboxylic acid (II), and in the meantime, more water formed will be distilled off.

Measure (a) of the inventive process includes the reaction of amine (I) with carboxylic acid (II). Said reaction can be a one-step or two-step reaction. Said reaction may include the intermediate formation or a salt (ammonium carboxylate) that thereafter condenses to form an amide, or it may proceed directly.

Measure (a) is performed at temperature and pressure conditions at which water and amine according to formula (I) are gaseous, which means that the pressure and temperature conditions are in a way that water and amine (I) is gaseous. Thus, e. g., if amine (I) is selected from diethyl amine and the pressure is selected to be normal pressure (atmospheric pressure, 1 bar) the reaction temperature is at least 105° C. and preferably in the range of from 130 to 230° C.

In one embodiment of the present invention, the reaction in measure (a) is carried out at a temperature in the range of from 130 to 230° C., the pressure being adjusted accordingly, preferably in the range of from 150 to 210° C.

In one embodiment of the present invention, the reaction in measure (a) is carried out at a pressure in the range of from 0.5 bar to 40 bar, preferably from atmospheric pressure to 10 bar, the temperature being adjusted accordingly.

The reaction of amine (I) with carboxylic acid (II) in measure (a) is being effected by contacting amine (I) and carboxylic acid (II). It is preferred to first charge the reactor that measure (a) is going to be performed in with a carboxylic acid (II). Said reactor may be charged with carboxylic acid (II) preferably being in the liquid form. However, as the case may be, it is also possible to charge carboxylic acid in solid form which may include a melting step before carrying out measure (a), and to then introduce amine (I), or to melt carboxylic acid (II) in the presence of amine (I). In one embodiment, carboxylic acid is charged as aqueous solution, and firstly, solvent water will be distilled off.

In one embodiment of the present invention, especially in embodiments where carboxylic acid is selected from α-hydroxyl $C_3$-$C_{12}$-carboxylic acids, carboxylic acid can contain some esters as impurity. This could be for example lactide and lactic acid oligomers in the case of lactic acid.

Preferably, the reaction in measure (a) is carried out under mixing, e.g., under stirring or by recirculation of the liquid. It is possible to introduce amine (I) in liquid form and to effect evaporation in the vessel in which the reaction is being performed but it is preferred to introduce amine (I) in the gas state (in gaseous form).

Preferably, the reaction in measure (a) is carried out batchwise or semi-batch-wise.

Measure (a) can be performed in a cascade reactor but it is preferred to perform measure (a) in a single vessel, e.g., in a tank reactor. Said vessel and preferably said tank reactor is equipped with—among others—a means for removing water in the gas state, a means for introducing carboxylic acid (II) and for introducing amine (I), and a means for reintroducing amine (I) according to measure (d), see below.

Preferably, said vessel is equipped with means for removing water in the gas state which usually contains some amine (I), and with means for separating water and amine (I), e.g., a distillation column, a fractionation column, and/or at least one condenser, or a combination of two or more fractionating columns, advantageously with one or two condensers.

In one embodiment of the present invention, said vessel is equipped with two fractionating columns and two condensers, adjusted at two different temperatures.

The reaction of carboxylic acid (II) with amine (I) can be performed in the presence of an organic solvent such as toluene or xylene but it is preferred to perform measure (a) without the use of any organic solvent. In such case, measure (b) will not require any organic solvent.

In one embodiment of the present invention, measure (a) is being performed under use of a catalyst. In another embodiment, measure (a) will be performed without catalyst.

In one embodiment of the present invention, measure (a) is being performed under use of an additive, e.g., a foam suppressor or anti-foam agent or an anti-oxidant such as but not limited to alkali metal hypophosphite. In an alternative embodiment, measure (a) will be performed without additives.

In measure (b), the water formed by the amide formation will be distilled off. During measure (b), water will be distilled of together with unreacted amine (I). Water can be distilled off with the majority of unreacted amine (I) or with all the excess of amine (I), or it can be distilled off together with only very small percentages of the amine (I). Distilling off will be effected by removing parts of the gas phase in the vessel and in particular in the tank reactor in which measure (a) is performed in. Said removal can be performed, e.g., by opening an exit or a valve from the vessel into a means for separating amine (I) from water. It is also possible to have a permanent exit open and to allow gaseous amine (I) and steam to leave the vessel that measure (a) is performed in and to make it go into the means for separating amine (I) from water.

The flow of gaseous materials (water, amine (I) can be enhanced by at least one pump (e.g. blower).

In measure (c), unreacted amine (I) and water distilled off in measure (b) are being separated. Said separation can advantageously be achieved with one distillation column, two distillation columns, one fractionating column, two fractionating columns, three or more distillation columns, three or more fractionating columns, or one or more membranes. The use of one or more distillation or fractionating columns is preferred. In particular, it is preferred to use one or two distillation columns in combination with one or more condensers or with one or more dephlegmators.

If one or more condenser are used in combination with fractionating or distillation columns it is preferred to operate said condenser(s) in a way that at least 90% by weight of the water that is distilled off will be removed from the gaseous stream, preferably at least 95% by weight. In one embodiment, the water that is distilled off will be removed completely, or up to 99.9% by weight of the water is removed.

It is preferred to remove the water from the mixture in measure (c) the in liquid form.

In case one or more fractionating columns are used, it is preferred to use such columns selected from plate columns and packed columns. Examples for plates comprised in plate columns are bubble cap plates, sieve plates, and valve plates. Examples for packing suitable for packed columns are random dumped packings and structured packings.

In case that in measure (c) a combination of at least one fractionating column or at least one distillation column with at least one condenser or at least one dephlegmator is used the reflux ratio is adjusted in a way that the reflux of water into the reaction mixture of measure (a) is as small as possible.

In one embodiment of the present invention, measure (c) is designed in a way that the fractionating column has in the range of from 2 to 40 equilibrium steps.

In a preferred embodiment of the present invention reflux ratio and equilibrium stages of column(s) combined with condenser(s) or dephlegmator are adjusted in a way that water can be disposed of without further purification, and amine (I) of 90% by weight purity or higher can be re-introduced into the reaction.

In one embodiment of the present invention, a membrane is used to separate water and amine.

By separating amine (I) from water, amine (I) is being recovered.

In measure (d), the amine (I) recovered according to measure (c) will be re-introduced into the reaction mixture in measure (a). Amine (I) can be re-introduced in liquid or in gaseous form. It is preferred to re-introduce amine (I) into reaction according to measure (a) in gaseous form.

In one embodiment of the present invention, one or more blowers are selected as means for re-introduction of amine (I) (compressors), especially roots blowers, together with a gas diffusor such as, e.g., a sparge ring.

In one embodiment of the present invention, gasification agitators are selected as means for re-introduction of amine (I), preferably gasification agitators with suction capability, without or in combination with a blower.

In one embodiment of the present invention, liquid jet nozzles are selected as means for re-introduction of amine (I). In this embodiment, the reaction vessel discussed in measure (a) can contain but does not necessarily require a stirrer.

In one embodiment of the present invention, liquid reaction mixture of measure (a) will be used to operate a liquid jet nozzle, e. g., as motive fluid (ejector).

The inventive process can be operated as a batch process, a semi-batch process or a continuous process. It is preferred to operate it as batch or semi-continuous process.

In case the inventive process is operated as batch or semi-batch process, the reaction will be terminated after conversion of all or of almost all, such as 90 to 99.9 mol-%, of carboxylic acid (II), preferably 93 mol-% or more.

After termination of the reaction, amide of carboxlic acid (II) and amine (I) can be recovered in excellent yield and good purity. For many applications, such amide can be used without further purification but it is possible, in the alternative, to purify it. Useful methods of purification are distillation, deodourization (stripping), decolourisation with, e.g., charcoal, or filtration over silica.

In the case that carboxylic acid (II) is bearing one or more alcoholic hydroxyl groups, only very little by-product generated by nucleophilic substitution of the alcoholic hydroxyl group by amine (I) can be detected, if at all, such as zero to 3.0 mol-%, in particular 0.1 to 1.5 mol-%, zero to 1.0 mol-%, in particular 0.001 to 0.5 mol-%, referring to total desired amide. Said nucleophilic substitution by-products usually have a very disadvantageous odour, and the presence of traces as such can be detected easily.

The invention is further illustrated by examples.
Parts mean parts by weight.

Example 1

Manufacture of N,N-dimethyl Lactamide

The following apparatus set-up was used: stirred tank reactor, heating system, on top an exit to the bottom of a fractionating column ("first column") with Sulzer packing (40 elements, 40.200 Sulzer M752Y), no reflux, followed by another fractionating column ("second column") (Sulzer packing, 22.250 Sulzer M752Y Elements), feed at the top, and connected to a condenser (20° C.) on top of the column. In the second condenser, water was condensed but dimethylamine remained in the gaseous state. The set-up also comprised a liquid jet nozzle (ejector pump) for re-introduction of dimethylamine gas into the tank reactor.

The tank reactor was charged with 60.0 parts racemic lactic acid (88% by weight aqueous solution) and 0.51 parts sodium hypophosphite. The tank reactor was evacuated. Dimethylamine was introduced into the tank reactor as a gas (measure (a.1)). Under heating, 104 mol-% of the theoretical amount of dimethylamine (27.39 parts) were introduced into to the reactor over 8.9 h after starting the dimethylamine addition a temperature of 170° C. and a pressure of 2.14 bar (absolute) were reached. In the meantime, water was removed from the reaction mixture—together with dimethylamine (measure (b.1))—by distillation and passed through the first column. In the second column, water and dimethylamine were separated (measure (c.1)). Gaseous dimethylamine was re-introduced through a loop with the liquid jet nozzle into the reactor (measure (d.1)). The acid value was monitored throughout the reaction (DIN 53402).

The reaction was continued for 37.5 hours during which the temperature was kept at 166° C. to 172° C. The pressure in the reactor was at 1.34 bar (absolute) at the end of measure (b.1). The acid value of the crude reaction product was 7.8 mg KOH/g at that time.

The crude product was stripped in a different vessel in order to remove low boiling by-products, e.g. the excess of dimethylamine. The stripped crude product contained 95.7% N,N-dimethyl lactamide (GC-analysis, by evaluating the area of the gas chromatogram).

Example 2

Manufacture of N,N-dimethyl Lactamide

The following apparatus set-up was used: stirred tank reactor, heating system, on top an exit to the bottom of a fractionating column ("first column") with Sulzer packing (20 elements, 20.200 Sulzer M752Y), reflux condenser, followed by another fractionating column ("second column") (Sulzer packing, 22.250 Sulzer M752Y Elements), feed at the top, and connected to a condenser on top of the column. In the second condenser, water was condensed but Dimethylamine remained in the gaseous state. The set-up also comprised a liquid jet nozzle (ejector pump) for the re-introduction of dimethylamine gas into the tank reactor.

The tank reactor was charged with 120 parts lactic acid (88% by weight aqueous solution) and 0.11 parts sodium hypophosphite. The tank reactor was evacuated. Dimethylamine was introduced into the tank reactor as a gas (measure (a.1)). Dimethylamine was initially added without heating. After 66% of the stoichiometric amount of DMA was added (over 7.5 h), the reaction mixture was heated to 170° C. At 168-176° C. reaction temperature and a pressure of 0.5-2.3 barg the rest of the DMA was added. In total 102 mol-% of the theoretical amount of dimethylamine (53.75 parts) were introduced into to the reactor over the time (finalized 51 h after the start of the DMA feed). In the meantime, water was removed from the reaction mixture—together with dimethylamine (measure (b.1))—by distillation and passed through the first column. In the second column, water and dimethylamine were separated (measure (c.1)). Gaseous Dimethylamine was re-introduced through a loop with the liquid jet nozzle into the reactor (measure (d.1)). The acid value was monitored throughout the reaction (DIN 53402).

The reaction was continued until an acid value of the crude reaction product of 10 mg KOH/g was reached. The total reaction time from the start of the DMA flow until the end was 68 h. The crude product contained 97.3% N,N-dimethyl lactamide (GC-analysis, by evaluating the area of the gas chromatogram).

The crude product was stripped by purging with nitrogen in order to remove low boiling by-products, e.g. the excess of dimethylamine. The yield of the stripped product was 135.8 parts Example 3

Manufacture of N,N-dimethyl C8/C10 Amide

The same equipment was used as in example 2.

The tank reactor was charged with 91.6 parts C8/C10 fatty acid (Edenor V85) and 0.11 parts sodium hypophosphite. The tank reactor was evacuated. Dimethylamine (DMA) was introduced into the tank reactor as a gas (measure (a.1)) and the mixture was heated to 179° C. Dimethylamine was added at a speed that the pressure stayed below 2.0 barg. Heating was applied to keep the reaction temperature at 196-198° C. In total 101 mol-% of the theoretical amount of dimethylamine (28.43 parts) were introduced into to the reactor over 9.2 h. In the meantime, water was removed from the reaction mixture—together with dimethylamine (measure (b.1))—by distillation and passed through the first column. In the second column, water and dimethylamine were separated (measure (c.1)). Gaseous Dimethylamine was re-introduced through a loop with the liquid jet nozzle into the reactor (measure (d.1)). The acid value was monitored throughout the reaction (DIN 53402).

The reaction was continued until an acid value of the crude reaction product of 6 mg KOH/g was reached. The total reaction time from the start of the DMA flow until the end was 12.7 h.

The crude product was stripped by purging with nitrogen in order to remove low boiling by-products, e.g. the excess of dimethylamine. The yield of the stripped product N,N-dimethyl C8/C10 amide was 102.4 parts.

The invention claimed is:

1. A process for making an amide of a carboxylic acid, the process comprising: reacting an amine of the formula (I)

$$H\text{—}NR^1R^2 \quad (I)$$

wherein $R^1$ and $R^2$ are the same or different, R1 comprising a $C_1$-$C_4$-alkyl, and $R^2$ comprising hydrogen or a $C_1$-$C_4$-alkyl, $R^1$ and $R^2$ being combined in a way such that the amine according to formula (I) has a lower boiling point than water, with a carboxylic acid with at least 3 carbon atoms per molecule, the carboxylic acid optionally comprising at least one alcoholic hydroxyl group per molecule, selecting a molar ratio of amine according to formula (I) to carboxylic acid in the range of from 1.5:1 to 1:1, the reaction step further comprising the following measures:

(a) reacting the amine according to formula (I) with the carboxylic acid at temperature and pressure conditions at which water and the amine according to formula (I) are gaseous, wherein the reaction is performed in a single reactor, (b) distilling off the water formed together with unreacted amine according to formula (I), (c) separating the unreacted amine according to formula (I) from the water and (d) re-introducing the unreacted amine according to formula (I) into the reaction mixture in measure (a).

2. The process of claim 1, wherein measures (a) and (b) are carried out without the use of any organic solvent.

3. The process of claim 1, wherein the reaction in measure (a) is carried out at a temperature in the range of from 130 to 230° C.

4. The process of claim 1, wherein the carboxylic acid comprises lactic acid.

5. The process of claim 1, wherein the amine according to formula (I) comprises methylamine, dimethylamine, ethylamine, diethylamine, n-propylamine, isopropylamine, diisopropylamine, n-butylamine, iso-butylamine, tert-butylamine, methyl n-propylamine, n-methyl-n-ethyl amine, or methyl iso-propylamine.

6. The process of claim 1, wherein the single reactor is connected to a fractionation column and a condenser.

7. The process of claim 1, wherein the single reactor is connected to a combination of two fractionation columns and two condensers.

8. The process of claim 1, wherein the step for re-introducing the unreacted amine according to formula (I) into the reaction mixture comprises using liquid jet nozzles.

9. The process of claim 1, wherein the carboxylic acid comprises caprylic acid, capric acid, or lauric acid and the amine comprises dimethylamine or diethylamine.

10. The process of claim 1, wherein the molar ratio of amine according to formula (I) to carboxylic acid is in the range of from 1.2:1 to 1:1.

* * * * *